US008105780B2

(12) United States Patent
Su et al.

(10) Patent No.: US 8,105,780 B2
(45) Date of Patent: Jan. 31, 2012

(54) DEVICE AND METHOD OF DETECTING MUTATIONS AND POLYMORPHISMS IN DNA

(75) Inventors: Xiaodi Su, Singapore (SG); Rudolf Robelek, Singapore (SG); Wolfgang Knoll, Singapore (SG); Sean O'Shea, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 551 days.

(21) Appl. No.: 10/948,275

(22) Filed: Sep. 22, 2004

(65) Prior Publication Data

US 2005/0164236 A1  Jul. 28, 2005

Related U.S. Application Data

(60) Provisional application No. 60/504,434, filed on Sep. 22, 2003, provisional application No. 60/534,366, filed on Jan. 6, 2004.

(51) Int. Cl.
*C12Q 1/68* (2006.01)
*C12P 19/34* (2006.01)
*C12M 1/34* (2006.01)
*C07H 21/04* (2006.01)
*G01N 33/50* (2006.01)

(52) U.S. Cl. .................... 435/6.11; 435/91.1; 435/287.2; 536/24.3; 702/20

(58) Field of Classification Search .................. None
See application file for complete search history.

(56) References Cited

U.S. PATENT DOCUMENTS

| | | | |
|---|---|---|---|
| 5,265,479 A | 11/1993 | Cook et al. | |
| 5,869,763 A | 2/1999 | Vig et al. | |
| 6,027,877 A | 2/2000 | Wagner, Jr. | |
| 6,051,379 A * | 4/2000 | Lescallett et al. | 435/6 |
| 6,114,115 A | 9/2000 | Wagner, Jr. | |
| 6,120,992 A * | 9/2000 | Wagner, Jr. | 435/6 |
| 6,162,610 A * | 12/2000 | Bronstein et al. | 435/7.92 |
| 6,284,463 B1 * | 9/2001 | Hasebe et al. | 435/6 |
| 6,329,147 B1 | 12/2001 | Wagner, Jr. | |
| 6,391,624 B1 * | 5/2002 | Megerle | 435/287.2 |
| 6,439,765 B2 | 8/2002 | Smith | |
| 2003/0008335 A1 | 1/2003 | Marx et al. | |
| 2004/0132029 A1 * | 7/2004 | Sussman et al. | 435/6 |

FOREIGN PATENT DOCUMENTS

| | | |
|---|---|---|
| EP | 0733126 B1 | 9/1996 |
| WO | WO 97/45555 A1 | 12/1997 |
| WO | WO 02/20832 A1 | 3/2002 |

OTHER PUBLICATIONS

Zhou, Xi Chun et al. Amplified microgravimetric gene sensor using Au nanoparticle modified oligonucleotides. 2000. Chemical Communications. pp. 953-954.*
Okahata, Yoshio et al. Kinetic Measurments of DNA hybridization on an oligonucleotide immobilized 27 MHz quartz crystal microbalance. 1998. Analytical Chemistry vol. 70, No. 7 pp. 1288-1296.*
Nollau, Peter et al. Methods for detection of point mutations performance and quality assessment. 1997. Clinical Chemistry 43:7 pp. 1114-1128.*
Okahata, Yoshio et al. Kinetic studies of sequence specific binding of GCN4-bZIP peptides to DNA strands immobilized on a 27 MHz quartz crystal microbalance. 1998. Biochemistry vol. 37, pp. 5666-5672.*
H.A. Behrensdorf, et al. "Rapid parallel mutation scanning of gene fragments using a microelectronic protein-DNA chip format", Nucleic Acids Research. 2002. pp. e64. vol. 30, No. 14.
C. Bellanne-Chantelot, et al. "Search for DNA sequence variations using a MutS-based technology". Mutation Research Genomics. 1997. pp. 35-43. vol. 382.
J. Brown, et al. "Affinity of mismatch-binding protein MutS for heteroduplexes containing different mismatches". Biochem. J. 2001. Pages 627-633. vol. 354.
E.J. Calvo, et al. "Measurement of Viscoelastic Changes at Electrodes modified with Redox with a Quartz Crystal Device". Faraday Trans. 1995. pp. 4083-4091. vol. 91, Issue 22.
K.T. Chong, et al. "Polyethylene-co-acrylic Acid as Coating for Biosensor Application: A Quartz Crystal Microbalance Study". Langmuir. 2002. Pages 9932-9936. vol. 18.
L.M. Furtado and M. Thompson. "Hybridization of complementary strand and single-base mutated oligonucleotides detected with an on-line acoustic wave sensor". Analyst. 1998. pp. 1937-1945. vol. 123.
M. Gotoh, et al. "Rapid method for detection of point mutations using mismatch binding protein (MutS) and an optical biosensor". Generic Analysis: Biomolecular Engineering. 1997. pp. 47-50. vol. 14.
S. Hagihara, et al. "Detection of guanine-adenine mismatches by surface plasmon resonance sensor carrying naphthyridine-azaquinolone hybrid on the surface". Nucleic Acids Research. 2004. pp. 278-286. vol. 32, No. 1.
A. Kobori, et al. "The SPR Sensor Detecting Cytosine-Cytosine Mismatches". J. Am. Chem. Soc. 2004. pp. 557-562. vol. 126.
B.G. Healy, et al. "Fiberoptic DNA Sensor Array Capable of Detecting Point Mutations". Analytical Biochemistry. 1997. pp. 270-279. vol. 251, Issue 2.
F. Hook, et al. "Variations in Coupled Water, Viscoelastic Propeties, and Film Thickness of a Mefp-1 Protein Film during Adsorption and Cross-Linking: A Quartz Crystal Microbalance with Dissipation Monitoring, Ellipsometry, and Surface Plasmon Resonance Study". Anal. Chem. 2001. pp. 5796-5804. vol. 73.
T. Liebermann. et al. "Complement hybridization from solution to surface-attached probe-oligonucleotides observed by surface-plasmon-field-eahanced fluorence spectroscopy". Colloids and Surfaces A: Physicochemical and Engineering Aspects. 2000. pp. 337-350. vol. 169.

(Continued)

*Primary Examiner* — Amanda Shaw
(74) *Attorney, Agent, or Firm* — Klarquist Sparkman, LLP

(57) ABSTRACT

There is provided a resonator sensor useful for detecting polymorphisms and mutations in DNA. The resonator sensor has a capture molecule immobilised on its surface, the capture molecule being either a probe DNA containing a reference sequence, or a mismatch binding molecule, and being capable of forming a probe DNA/target DNA/mismatch binding molecule complex on the surface of the resonator. A method for detecting mutations in a target DNA, including single nucleotide polymorphisms, is also provided.

42 Claims, 9 Drawing Sheets

OTHER PUBLICATIONS

M.H. Lamers, et al. "The crystal structure of DNA mismatch repair protein MutS binding to a G-T mismatch". Nature. Oct. 12, 2000. pp. 711-717. vol. 407.

K Nakatani, et al. "Scanning of guanine-guanine mismatches in DNA by synthetic ligands using surface plasmon resonance". Nature Biotechnology. Jan. 2001. pp. 51-55. vol. 19.

P. Nilsson, et al. "Analysis of DNA sequency using biosensors". Laboratory Methods for the Detection of Mutations and Polymorphisms in DNA (edited by Graham R. Taylor). c1997. pp. 253-261 (Chapter 23). CRC Press, Boca Raton New York.

M. Rodahl, et al. "Simultaneous frequency and dissipation factor QCM measurements of biomolecular adsorption and cell adhesion". Faraday Discuss, 1997. pp. 229-246. vol. 107.

H.B. Sun and H. Yokota. "MutS-Mediated Detection of DNA Mismatches Using Atomic Force Microscopy". Analytical Chemistry. Jul. 15, 2000. pp. 3138-3141. vol. 72, No. 14.

P.Wittung-Stafshede, et al. "Detection of point mutations in DNA by PNA-based quartz-crystal biosensor". Colloids and Surfaces A: Physicochemical and Engineering Aspects. 2000. pp. 269-273. vol. 174.

A.M. Wieczorek, et al. "Structure-based rescue of common tumor-derived p53 mutants". Nature Medicine. Oct. 1996. pp. 1143-1146. vol. 2, No. 10.

Y. Zhang, et al. "Direct detection of mutation sites on stretched DNA by atomic force microscopy". Surface and Interface Analysis. 2002. pp. 122-125. vol. 33, Issue 2.

M. Nagel, et al. "A functionalized THz sensor for marker-free DNA analysis". Phys. Med. Biol. 2003. pp. 3625-3636. vol. 48.

E.V. Olsen, et al. "Specific and selective biosensor for Salmonella and its detection in the environment". Journal of Microbiological Methods. 2003. pp. 273-285. vol. 53.

M. Su, et al. "Microcantilever resonance-based DNA detection with nanoparticle probes". Applied Physics Letters. May 19, 2003. pp. 3562-3564. vol. 82, No. 20.

Keller, W. et al., "Crystal Structure of a bZIP/DNA Complex at 2.2 Å: Determinants of DNA Specific Recognition", J. Mol. Biol., 1995, pp. 657-667, vol. 254.

Kalodimos, C.G. et al., "Structure and Flexibility Adaptation in Non-specific and Specific Protein-DNA Complexes", Science, 2004, pp. 386-389, vol. 305.

* cited by examiner

DEVICE AND METHOD OF DETECTING MUTATIONS AND POLYMORPHISMS IN DNA

CROSS-REFERENCE TO RELATED APPLICATIONS

The present application claims priority from U.S. provisional patent application No. 60/504,434, filed on Sep. 22, 2003 and U.S. provisional patent application No. 60/534,366, filed on Jan. 6, 2004, the contents of which are hereby incorporated herein by reference.

FIELD OF THE INVENTION

The present invention relates generally to devices and methods for detection of mutations and polymorphisms in DNA, and particularly to use of mismatch binding proteins and ligands for same.

BACKGROUND OF THE INVENTION

A polymorphism is a variation in genetic sequence in which an individual's genetic sequence at a given location in the genome varies from the sequence commonly found in a population. Polymorphisms can be induced by mutagens, or they may be naturally occurring in a population. Presence of a polymorphism in an individual's DNA can often be used as a disease marker, since particular polymorphisms tend to be linked to certain diseases. Polymorphisms include single or multiple base substitutions, insertions or deletions. In human molecular and medical genetics, the vast majority of mutations and sequence polymorphisms in DNA result from single base substitution and small additions and deletions. The efficient, accurate and rapid detection of these variations is very important in the prediction and diagnosis of disease, forensic medicine, and public health.

Most methods for detection of genetic alternations consisting of one or a few bases involve hybridization between a standard nucleic acid (DNA or RNA) and a test DNA: the mutation may be revealed as a mispaired or unpaired base in a heteroduplex. Detection of these mispaired or unpaired bases has been accomplished by a variety of methods (Taylor, G. R., *Laboratory Methods for the Detection of Mutations and Polymorphisms in DNA*, CRC Press, (1997)), including denaturing gradient gel electrophoresis, enzyme or chemical mismatch cleavage, and direct sequencing of polymerase chain reaction products. These methods typically involve time-consuming or technically complicated methods that are not suitable for handling a large number of samples at one time, such as gel-electrophoresis and/or staining procedure. Some of the methods require that the exact location of the mutation be known, and the results can be difficult to interpret when the target DNA is heterozygous for the mutation in question. Thus, such techniques are not practical for use in screening of large numbers of samples for polymorphisms.

Other methods of detecting genetic alterations include chip- or sensor-based detection techniques, including methods using DNA microarrays or silicon-based DNA chips, and electrochemical, thermometric, microgivmetric, magnetic or optical methods, including fiberoptic methods. These techniques generally involve immobilization of a DNA probe strand to a support and subsequent hybridization of test DNA to the immobilized probe. Mutations that result in mispaired or unpaired bases in the hybridized heteroduplex molecule are detected by monitoring the hybridization affinity of the test DNA to the immobilized probe DNA, as these alternations affect the hybridization affinity (Knoll et al., *Colloids and Surface A: Physicochemical and Engineering Aspects* (2000) 169:137; Healy et al. *Anal Biochem* (1997) 251(2): 270-279) and thus produce different signal outputs, depending on the method use. The discrimination of the hybridization profiles of a mutant strand from wild-type DNA typically relies on the use of high stringency hybridization conditions, for example optimized hybridization temperature based on the melting properties (Tm) of the strands (Wittung-Stafshede P. et al., *Colloid Surface A*, 174: 269-273 (2000); Furtado, L. M. et al., *Analyst*, 123: 1937-1945 (1998)), high stringency buffer (Chong K. T. et al., *Langmuir*, 18:9932 (2003)), or both (Nilsson, P., et al, *Laboratory Methods for the Detection of Mutations and Polymorphisms in DNA*, Graham R. Taylor CRC Press, Boca Raton N.Y. 1997). These methods, however, are unsuitable for scanning wide regions of DNA (a capability essential for the detection of genomic polymorphisms) as single base substitutions or deletions result in very small differences in the hybridization affinity. As well, the detection sensitivity of these methods is in the level of the micromolar or sub-micromolar range, which is far below the limit required for disease diagnosis.

MutS, a DNA mismatch binding protein, has been used to detect mismatches in DNA samples. Wagner (U.S. Pat. Nos. 6,027,877, 6,114,115, and 6,329,147) describes methods in which labelled DNA is contacted with MutS protein for detection of any mismatches in the DNA sample. The MutS is immobilized on a chromatography column. Since these methods use chromatography methods, they are not well adapted to parallel analysis of multiple samples.

Thus, there is a need for a method of detecting mutations and polymorphisms in a DNA sample that is accurate, fast and easy to use, is suited for high-throughput analysis, and which enables identification of the location and nature of the mutation within a target DNA.

SUMMARY OF THE INVENTION

The present invention provides a resonator sensor having an immobilized capture molecule, either probe DNA containing non-disease DNA sequence, or a mismatch binding molecule. The resonator sensors described herein are useful for detection of a mutation or a polymorphism in target DNA. The present methods are advantageous in that they are simple, requiring relatively simple instrumentation, and do not involve gel electrophoresis or staining techniques.

The methods may incorporate nanoparticle- and enzyme-based signal amplification techniques to achieve ultra-sensitive gene mutation detection.

Furthermore, as resonator sensors are easy to miniaturize and automate, the present methods may be adapted for resonator array techniques, for high throughput and rapid screening of multiple DNA samples or multiple mutations at one time.

In one aspect, the present invention provides a method of detecting a mutation in a target DNA comprising obtaining a first measurement of a resonance parameter of a resonator sensor, said resonator sensor having a vibrating element, said vibrating element having a surface, and a probe DNA immobilised on said surface, said probe DNA hybridized with a target DNA; contacting the hybridized probe DNA and target DNA with a mismatch binding molecule; obtaining a second measurement of the resonance parameter of the resonator sensor; and comparing the first and second measurement of the resonance parameter.

In another aspect there is provided a method of detecting a mutation in a target DNA comprising obtaining a first measurement of a resonance parameter of a resonator sensor, said resonator sensor having a vibrating element, said vibrating element having a surface, and a mismatch binding molecule immobilised on said surface; contacting the mismatch binding molecule with a hybridized probe DNA and target DNA; obtaining a second measurement of the resonance parameter of the resonator sensor; and comparing the first and second measurement of the resonance parameter.

In another aspect there is provided a resonator sensor comprising a vibrating element having a surface; a probe DNA immobilized on said surface, said probe DNA capable of hybridizing with a target DNA; an excitation source for vibrating said vibrating element; and a detector for detecting a change in vibration of said vibrating element indicative of binding a mismatch binding molecule to said probe DNA when hybridized with said target DNA to form a heteroduplex DNA.

In a further aspect there is provided a resonator sensor comprising a vibrating element having a surface; a mismatch binding molecule on said surface, said mismatch binding molecule capable of binding a heteroduplex DNA; an excitation source for vibrating said vibrating element; a detector for detecting a change in vibration of said vibrating element indicative of binding said heteroduplex DNA to said mismatch binding molecule.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
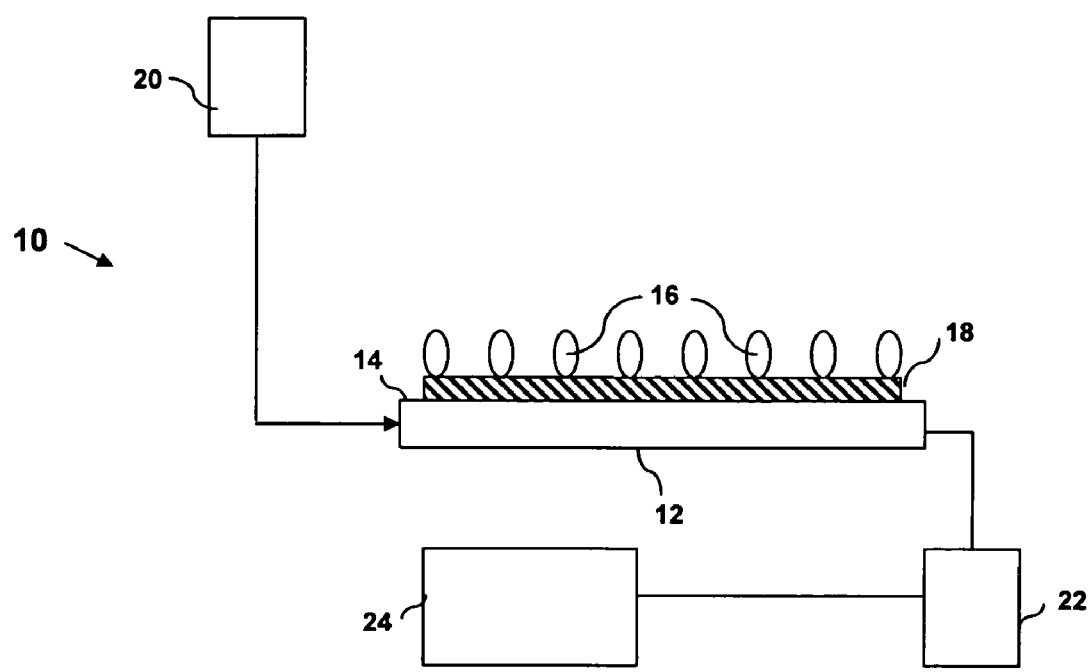
FIG. 1 is a block schematic diagram of a resonator sensor detecting a polymorphism or mutation of a target DNA, exemplary of an embodiment of the present invention.

DNA polymorphisms are genetic variations in a population that occur at certain locations in the genome. Confirmation that an individual carries a particular polymorphism can often be used as an indicator of disease or that the individual is a carrier of a disease gene.

Single base substitutions, and small insertions and deletions associated with a DNA polymorphism, for example of 1 to 4 bases, can be detected by hybridizing test DNA with a reference DNA and contacting with a molecule that binds mismatch DNA, where either the reference DNA or the mismatch binding molecule is immobilized on a resonator sensor.

"Mismatch DNA" or "heteroduplex DNA" refers to DNA which includes one or more mismatch base pairings. A mismatch base pairing refers to a specific pair of opposing bases, in the context of a DNA duplex, which cannot form one of the hydrogen-bonded base pairs, T with A or G with C. Heteroduplex DNA includes double-stranded DNA in which one or more bases in one strand does or do not complement the base or bases in the opposing strand, as well as double-stranded DNA in which one or more bases of either strand does or do not have an opposing base, due to an insertion or deletion in one strand as compared to the opposing strand. In contrast, homoduplex DNA refers to double-stranded DNA in which each strand is a complete complement of the other strand, and each base forms a hydrogen-bonded base pair with an opposing base.

"Target DNA" refers to a test DNA or sample DNA that is desired to be screened for mutations relative to a reference DNA sequence, such as a single nucleotide polymorphism or small insertions or deletions, for example up to 4 bases in length.

Various mismatch binding molecules will bind to heteroduplex DNA. DNA mismatch repair systems employ a family of mismatch binding proteins (MBP) that recognize and bind strongly and preferentially to heteroduplex DNA, and weakly to fully complementary DNA and single-stranded DNA. For example, the MutS protein has been identified as such a component of the *Escherichia coli* mismatch repair system (Lamers et al., *Nature* (2000) 407:711-717). Analogous proteins are known in other bacterial species including MutS protein from *Salmonella typhimurium* and *Thermus aquaticus*, and the HexA protein from *Streptococcus pneumoniae*. As well as MBPs, synthetic mismatch binding ligands ("SMBL") are also able to recognize specific mismatches based on the design of the molecules (Nakatani et al., *Nature Biotech.* (2001) 19:51; Hagihara et al., *Nuc. Acids Res.* (2004) 32: 278-286; Hagihara et al., *J. Am. Chem. Soc.* (2004) 126: 557-562). For example, dimeric naphthyridine recognizes and binds to a G:G mismatch, a naphthyridine-azaquinolone hybrid binds to and recongnizes a G:A mismatch and dimeric aminonaphthyridine recognizes and binds to a C:C mismatch.

Thus, a mismatch binding molecule can recognize and bind to heteroduplex DNA to form a mismatch binding molecule/heteroduplex DNA complex.

As will become apparent, a resonator sensor exemplary of an embodiment of the present invention may be used to detect the mismatch binding molecule/heteroduplex complex. Either the heteroduplex DNA or the mismatch binding molecule is immobilized on a vibrating element of the resonator sensor. As detailed below, by monitoring the frequency spectrum of the vibrating element, mutation or polymorphism in the target DNA may be detected.

Resonator sensors are known in the art, and include bulk acoustic wave devices, thickness shear mode quartz crystal microbalances ("QCM"), surface acoustic wave devices ("SAW"), tuning forks, flexural wave plates, piezoelectric thin films, micro-electromechanical systems ("MEMS") resonators, membranes, bridges, suspended masses and cantilevers, any of which are suitable for use in the resonator sensor or methods presented herein.

To this end, a schematic of a resonator sensor 10, exemplary of an embodiment of the present invention, is illustrated in FIG. 1. Resonator sensor 10 includes a vibrating element 12 and an excitation source 20. Element 12 may be driven to vibrate through the application of an electromotive or similar force, from source 20. At a particular frequency of excitation source 20, element 12 will vibrate more efficiently than at other frequencies. This frequency is referred to as the resonant frequency of sensor 10.

The type of excitation source 20 used will depend in part on the nature of sensor 10. For example, a resonator sensor 10 that includes a quartz crystal vibrating element 12 can be made to oscillate by placing the crystal in a simple electrical feedback circuit. Most piezoelectric sensors can be driven in this way. The excitation source for other sensors, for example, silicon resonators, may be a driving electrostatic field placed near the silicon device. Alternatively, the excitation source 20 may include a device for creating an electric field, in combination with a small piezoelectric plates placed under a silicon resonator sensor, which can then be driven by oscillations of the piezoelectric plate. Excitation source 20 may alternatively use magnetic, thermal, or acoustic energy to drive vibrating element 12.

Now, vibrating element 12 may receive a sample of interest. Measuring the frequency response of sensor 10 including the sample of interest, allows physical characteristics of the sample of interest to be assessed.

The resonant frequency of sensor 10 will depend on the mass of the vibrating element 12 and any attached sample. An increase in the mass, for example as a result of an additional sample being attached to the vibrating element, will cause the resonant frequency to shift.

In the depicted embodiment, vibrating element 12 includes a surface 14, suitable for immobilizing a capture molecule 16. Surface 14 may be made of metal, polymer, silicon, glass or quartz. Optionally, surface 14 is coated with an additional layer 18. Layer 18 is composed of an activated substance, or a substance which may be readily activated or functionalized so as to be capable of reacting with capture molecule 16, to facilitate immobilization of the capture molecule on vibrating element 12. The layer 18 may be, for example, a metal, for example gold or indium tin oxide, or it may be a polymer film, including for example, nitrocellulose, polystyrene, polyethylene, or nylon. An activated layer contains appropriate functional groups or atoms for chemically reacting with functional groups or atoms within or attached to capture molecule 16.

Now, capture molecule 16 may be a probe DNA comprising a reference DNA sequence and which is capable of binding with target DNA that is to be screened for mutations. Probe DNA may, for example, be single-stranded DNA, and may include a non-disease genetic marker sequence that is to be tested for mutation in the target DNA, for example a polymorphism. The probe DNA may alternatively contain a sequence that is to be screened against target DNAs collected from a population, so as to determine if such a sequence is a site for a polymorphism, or a site for a disease marker. The probe DNA will contain the control sequence, for example a reference sequence or a non-disease sequence, for the particular mutation that is to be detected, and can encompass a site that tends to be mutated in a portion of a population, and that for which mutations at that site may be associated with a particular disease state.

As used herein, a genetic marker is a given nucleotide sequence that occurs at a particular genetic loci, and which can be used as a reference point for mapping or identifying other genetic sequences. A disease marker is a genetic marker whose occurrence in an individual tends to be associated with a particular disease, or to be an indicator of a predisposition to develop a particular disease or that the individual is a heterozygous carrier of a disease gene. In contrast, as will be understood, a non-disease genetic marker sequence is a sequence that itself is not associated with a disease state or a predisposition to develop a disease. However, a mutation in such a sequence may lead to a disease state or a predisposition to develop a disease.

For example, the probe DNA may include the non-disease sickle cell genetic marker in the β-globin gene, or it may comprise a non-disease genetic marker involved in atherosclerosis, heart disease, diabetes, cystic fibrosis, Alzheimer's disease or cancer, for example, breast cancer. Other examples of genetic markers include those associated with the p53 gene, which is involved in regulation of apoptosis and defence against uncontrolled cell proliferation. Single nucleotide polymorphisms of certain p53 gene loci are very often directly related to a high probability of tumorigenesis (Wieczorek A M, et al. *Nat. Med.* (1996) 2(10):1143-6.).

The probe DNA may be synthesized chemically, or may be produced by amplification methods, such as polymerase chain reaction methods, from a template DNA. If amplification methods are used, high stringency techniques are preferred to minimize the occurrence of mutations or errors in individual molecules of the probe DNA. The probe DNA conveniently can be a length of DNA that can be produced en masse having a given sequence.

Chemical synthesis methods and amplifications methods for producing DNA will be understood by a skilled person and are described in standard texts and manuals, for example, Sambrook et al. in Molecular Cloning: A Laboratory Manual, 3$^{rd}$ Edition, Cold Spring Harbour, Laboratory Press. For example, standard phosphoramidite chemical ligation methods may be used to synthesize the primer in the 3' to 5' direction on a solid support, including using an automated nucleic acid synthesizer. Alternatively, high fidelity polymerase chain reaction may be performed using non-disease DNA as a template, along with primers that hybridize to sequences flanking the site of the polymorphism that is to be detected by the present method. If desired, the amplified product may be subsequently sequenced to confirm the sequence of the probe DNA.

The length of the probe DNA may be chosen to be any length so as to allow for regions of the probe to hybridize with regions of the target DNA flanking the sequence that is to be tested for mutation. For example, the probe DNA may be a short oligonucleotide, for example 20 to 30 bases in length. A skilled person will understand that if the probe DNA is too short, it will be very sensitive to temperature variations, and may not properly hybridize to target DNA, even at low temperatures. Thus, the probe DNA should be designed to be long enough so as to have a melting temperature when hybridised with target DNA that is sufficiently higher than the temperature at which the detection of binding of a mismatch binding molecule is to be performed, so as to maintain the DNA as a duplex during detection. Alternatively, the probe DNA may be a longer DNA fragment, for example, 50 to 100 bases in length. Preferably, the DNA probe is approximately 50 bases in length. The maximum length of the probe DNA is not limited provided DNA of that length can be synthesized without introducing errors into the sequence. For example, longer DNA fragments may be produced using high fidelity PCR amplification. A skilled person will be able to calculate the temperature at which a given sequence of DNA will hybridize with its complementary strand, and will understand that if the probe DNA is too short, it may not have enough sequence specificity and may bind to a number of sites in target DNA. If a probe is too long, it may include a number of mutations or polymorphisms in the target DNA.

Furthermore, the probe DNA may be designed such that the polymorphism or mutation that is to be detected is located toward the centre of the probe, rather than toward either end of the probe. This will allow for a longer portion of hybridized region on either side of the polymorphism or potential mutation sequence when the probe DNA is hybridized to the target DNA, which may facilitate recognition of heteroduplex DNA by a mismatch binding molecule. If any mismatch is to be detected using the MutS protein, the mismatch should be located sufficiently in from either end of the probe DNA so as to allow MutS to recognize and bind to the mismatch pairing.

Alternatively, capture molecule 16 immobilized on surface 14 may be a mismatch binding molecule. The mismatch binding molecule is a molecule that specifically binds to unpaired nucleotides in duplex DNA. The mismatch binding molecule may be a mismatch binding protein, for example MutS protein from *Escherichia coli, Salmonella typhimurium* or *Thermus aquaticus*, or HexA protein from *Streptococcus pneumoniae*. Alternatively, the mismatch binding molecule may be a synthetic mismatch binding ligand that binds to a specific mismatch base pairing, for example dimeric naphthyridine which recognizes and binds to a G:G mismatch. Other mismatch binding molecules will be apparent to those of ordinary skill.

The capture molecule 16 is immobilized on surface 14 or optionally on layer 18 that is deposited on surface 14, using standard methods known in the art. Depending on the material from which surface 14 or layer 18 is formed, a skilled person will understand the corresponding chemistries for covalent or non-covalent attachment of capture molecule 16. For example, on glass, quartz, and silicon, silane chemistry is frequently used to immobilize molecules on the surface or layer, and thiol chemistry is more suitable to introduce functional groups on a gold surface or layer.

For example, where the capture molecule is a probe DNA, one end of the probe DNA may be modified with a reactive functional group, such as a thiol, amino, carboxylic acid, hydroxyl, phenol or phosphate group, which may react with surface 14 of the vibrating element, such as a metal surface, so as to form a bond between the probe DNA and the surface of the vibrating element. A metal surface may be functionalized so as to make it reactive. For example, a metal surface may be treated with a compound such as propyl amino silane, or an amino-terminated thiol, providing the metal surface with reactive amino groups that can then react with suitable functional groups on the probe DNA. Preferably, the attachment of the probe DNA to the surface of the vibrating element is robust, so as to withstand the conditions used to rinse unhybridized target DNA and unbound mismatch binding molecule from the resonator sensor between steps of the present method, as well to withstand the conditions used to regenerate the resonator sensor with immobilized probe DNA between uses with different target DNAs.

The mismatch binding molecule may be immobilized on surface 14 or layer 18 using the same techniques as described above for immobilization of the probe DNA. Immobilization should be done in a manner that does not disrupt the ability of the mismatch binding molecule to specifically bind to heteroduplex DNA. For example, the MutS protein binds to mismatch DNA exclusively through its N-terminal mismatch-recognition domain. Thus, the immobilization may be designed to occur at the C-terminal residues of the protein, leaving the N-terminal domain available for binding to heteroduplex DNA.

When immobilizing the mismatch binding molecule, the mismatch binding molecule may be pre-incubated with a heteroduplex DNA in solution to form a mismatch binding molecule/DNA complex, which may then be immobilized onto the resonator sensor. The heteroduplex DNA may then be released from the mismatch binding molecule, such that the resonator sensor with immobilized mismatch binding molecule is regenerated and available for use in detecting mutations in a target DNA. This approach helps to minimize disruption of the mismatch binding molecule during immobilization on surface 14. This approach may be preferred when the mismatch binding molecule is a protein.

The capture molecule 16 may be immobilized by first coating the surface of the resonator sensor with layer 18, for example, a thin layer of a polymer film that binds the capture molecule 16 non-specifically, for example nitrocellulose, polystyrene, polyethylene, or nylon. The polymer should provide a suitably stable and strong attachment of the capture molecule 16 to the resonator sensor without destroying the ability of a mismatch binding molecule to bind to heteroduplex DNA, where the capture molecule 16 is either probe DNA or mismatch binding molecule. This method is useful when the capture molecule 16 is a mismatch binding molecule, particularly a mismatch binding protein, since proteins easily adsorb onto polymers such as nitrocellulose, polystyrene, polyethylene or nylon, through physical adsorption or hydrophobic interaction at an appropriate pH, incubation temperature, and incubation time, as will be understood by a skilled person.

A spacer molecule or molecules may be used to immobilize the probe DNA or the mismatch binding molecule onto surface 14. For example, a spacer molecule having a reactive functional group at one end and an affinity binding molecule covalently attached at the other end may be reacted with the surface of the vibrating element, such that the spacer molecule is bound to the resonator sensor via the reactive functional group, leaving the affinity binding molecule free. An affinity binding molecule is any molecule that interacts with another molecule through a specific interaction, such as either half of a receptor/ligand pair which bind to each other through a specific, non-covalent affinity interaction. For example, the affinity binding molecule may be biotin, streptavidin, avidin, an ATP analogue, an ATP binding domain, imidazole, digoxigenin or a 6-histidine peptide. A molecule that recognizes the affinity binding molecule may be attached to one end of the probe DNA or the mismatch binding molecule, so as to immobilize the probe DNA or the mismatch binding molecule to the resonator surface through the interaction with the affinity binding group. Alternatively, a second spacer molecule can be used. A second spacer molecule is a molecule that binds to the affinity binding molecule immobilized on the resonator surface, for example through a complementary affinity binding molecule attached to the second spacer molecule, and with the probe DNA or the mismatch binding molecule, or a group that is attached to one end of the probe DNA or the mismatch binding molecule, through a second site on the second spacer molecule, for example, through a reactive functional group such as an amine or carboxylate.

Alternatively, the spacer molecule may be a bi-functional small molecule that functions as a cross-linker and which has two reactive sites. For example, glutaraldehyde or imidates may be used to link a free amino group on the resonator surface with a free amino group on the probe DNA or mismatch binding molecule. Preferably, the amino groups on the resonator sensor and the probe DNA or mismatch binding molecule are primary amino groups.

For example, the surface of the vibrating element may be reacted with a thiol-biotin molecule that has a free thiol group at one end, to react with a metal layer, and a biotin moiety at the other end. Streptavidin, which forms a tetramer of four subunits with four biotin binding sites per assembled tetramer, is then used as a second spacer molecule and binds to the biotin residues that are immobilized on surface 14 and the probe DNA which has a biotin moiety attached at one end. Streptavidin has a very strong binding affinity for biotin, and is able to withstand stringent buffer conditions, making the biotin-streptavidin interaction a convenient and robust method of immobilizing the probe DNA onto the resonator sensor surface.

In another example, sulfosuccinimido-biotin or maleimide-biotin may be used as a spacer molecule. The reactive functional group, either the succinimide ester or the maleimide group will react with free amino or thiol groups, respectively, on surface 14 or layer 18, and the biotin affinity molecule on the other end of the spacer will be free to bind with an avidin or streptavidin group that may be attached to one end of capture molecule 16, either directly or through a second spacer molecule such as a second biotin molecule covalently attached at one end to capture molecule 16.

A motion sensor 22 may detect the vibration of vibrating element 12. Motion sensor 22 may for example be a non-contact optical sensor. Alternatively, in order to induce mechanical motion and to sense such motion, both the excitation source 20 and the resonator sensor 10 may include piezoelectric elements. Further, the drive and the sensor may be combined or have common parts. For example, a piezoelectric transducer may be mounted on vibrating element 12 for driving the vibration and for sensing the vibration.

Motion sensor 22 is coupled to a detector 24, which has computational ability to processes the information detecting by motion sensor 22, thereby measuring characteristics of the vibration of vibrating element 12 and determining the frequency response of the vibrating element. Detector 24 may be an instrument such as a spectrum analyser, a lock-in amplifier, a network analyser, a phase locked loop, or a counter/timer. The type of instrument used will depend on the desired degree of sensitivity of the measurement and on the type of resonator sensor used.

As is known to persons of skill in the art, characteristics of the vibration of vibrating element 12 that may be affected by a sample attached to surface 14 include resonant frequency, impulse response, resonance amplitude, damping, quality factor, energy dissipation, phase, response spectrum, and sharpness of resonance. A skilled person will understand that phase is calculated by comparing the output signal to the drive signal. The measured oscillation spectrum may be expressed as a plot of amplitude versus frequency. The sharpness of the resonance peak ("Q factor") is represented using the frequency range measured as width of the resonance peak at half the maximal height of the peak.

In use, to determine the resonance frequency response a baseline resonant frequency response of vibrating element 12 is measured before any sample is applied to the sensor 10. On the basis of a stable baseline, the sample to be tested is applied. The shift of the resonance response parameters will then be recorded.

Therefore, a change in the frequency response of vibrating element 12 can be observed upon formation of a mismatch binding molecule/heteroduplex DNA immobilized at the surface 14, if a mutation is present in the target DNA. As the mass loaded on vibrating element 12 is increased, such as by the complexing of a mismatch binding molecule to an immobilized heteroduplex DNA, the resonant frequency will shift to a lower frequency, allowing for detection of any binding of the mismatch binding molecule to heteroduplex DNA. Amplitude and Q factor will also decrease, since the immobilized heteroduplex and mismatch binding molecule will have a dissipative effect on the resonance of vibrating element 12.

Generally, damping and energy dissipation are reflective of the viscoelastic properties of a resonating body. Thus, when the mass loaded onto surface 14 results in changes in viscoelastic properties of the combine mass of surface 14 plus additional immobilized sample, such changes will be reflected in both the resonant frequency and Q factor. The effect on resonant frequency may be relatively small for certain resonator sensor types, such as high sensitivity resonator sensors, and is observed as a shift in frequency in response to stress applied at the surface of the resonator sensor. The major effect of viscoelastic changes is to change the Q factor of the resonator.

The damping of vibrating element 12 and any attached sample of interest can be used to indicate the position of the mutation relative to the sequence of the probe DNA. Damping relates to the decay of the vibration over time, and can be evaluated by measuring energy dissipation, motional resistance and Q factor in driving the resonator sensor 10 (Rodahl et al., *Faraday Discuss* (1997) 107: 229-246; Calvo et al., *Faraday Trans*. (1995) 91:4083-4091).

For example, the energy dissipation and motional resistance are influenced by how closely the mismatch binding molecule is located to the surface 14 of element 12. Thus, the closer the mutation site is to the end of a probe DNA that is immobilized onto the vibrational element 12, the lower the amount of damping should be that is observed upon binding of a mismatch binding molecule. Thus, measurement of these parameters, for example a change of dissipation factor measured using a QCM-D resonator sensor, can be used to identify the mutation site. Thus, the induced energy loss per unit mass loaded at the surface ($\Delta D/\Delta f$) can be used as an indicator of the relative distance of a mismatch in the heteroduplex from the surface 14 of sensor 10. The QCM-D technique is an extension of the traditional QCM techniques in the time-domain. The technique measures frequency, f, and energy dissipation, D, by periodically switching off the driving power over the crystal and recording the decay of the damped oscillation. The time constant of the decay is inversely proportional to D, and the period of the decaying signal gives f, allowing for measurement of $\Delta D/\Delta f$.

Resonator sensor 10 can also respond to changes of mechanical properties of the material contacting the surface of the sensor. For example, the stiffness of the material loaded on the surface 14 or layer 18 can be measured. A heteroduplex DNA/mismatch binding molecule complex immobilized on surface 14 or layer 18 will have a different stiffness depending on the manner of formation of the complex. For example, if an MBP such as MutS is used, the influence on the damping property factors by the binding of the mismatch binding molecule will vary depending on whether the binding is specific due to binding to a mismatch pairing, or whether it is non-specific due to interactions with the DNA backbone. MutS can bind to homoduplex in a sequence-non-specific manner, forming a relatively loosely structured complex, leading to greater energy dissipation upon vibration of vibrating element 12. The degree of energy dissipation is detectable by measuring energy loss per unit mass loaded onto surface 14 or layer 18 ($\Delta R/\Delta f$, where R is also reflective of the damping of the system). For example, a heteroduplex DNA/MutS complex will form a fairly tight structure due to the strong hydrogen bond interactions and the bending of the DNA by the bound protein, which results in a smaller energy loss by sensor 10 during vibration. Basically, the Young's modulus of the composite resonator (composite=the resonator+the adsorbed material) can change and this will lead to changes in the frequency response.

The resonator sensor 10 described above is useful for detecting mutations in a target DNA where the target DNA contains a sequence that is generally complementary to the probe DNA sequence, but which generally complementary sequence has one or more substitutions, insertions or deletions as compared to the sequence of the probe DNA. Sample may be applied to surface 14 using a liquid cell, which may be a flow cell, as is known in the art, or liquid may be pipetted directly onto surface 14, either manually or using an automated system. A stable baseline is first generated using buffer in the absence of any sample, after which the sample is added. The liquid cell can form either a flow through liquid or stand still liquid.

Thus, in one embodiment there is provided a method of detecting a mutation in a target DNA in which a capture molecule 16 immobilized on a resonator sensor, for example resonator sensor 10, allows for detection of formation of a heteroduplex DNA between probe DNA and target DNA through binding of a mismatch binding molecule.

For example, capture molecule 16 may be a probe DNA which is immobilized on a resonator sensor, like sensor 10, and which is hybridized with the target DNA. The hybridized probe DNA and target DNA is then contacted with a mismatch binding molecule such that the mismatch binding molecule will bind to the hybridized DNA if there is a mismatch between the strands. The resonance parameters of the resonator sensor are measured to determine if the mismatch binding molecule has bound to the hybridized DNA.

The site that is to be tested for mutation in the target DNA may be a single nucleotide, or it may be a longer sequence, for example, up to 4 base insertion, deletion or substitution, in the context of a sequence that is otherwise complementary to the probe DNA sequence.

Standard techniques for isolation of DNA from a cell sample are known in the art. Generally, cells are lysed and insoluble cell debris is removed, for example by centrifugation. DNA kits including columns for extracting DNA are commercially available. Alternatively, DNA can be extracted from a cell lysate using organic solvent extraction techniques followed by precipitation methods to isolate the DNA.

The target DNA may be DNA obtained from an individual, for example a patient including a human patient, which is desired to be tested for the presence of DNA mutations or polymorphisms in its genetic material. The DNA may be obtained from any cells of the individual, including blood, skin, liver, kidney, lung or breast cells. DNA may be obtained from a cancerous mass of a patient, such as a tumour including a solid tumour, in order to detect mutations that may be specific to the tumour but which may not be present in non-cancerous cells of the patient. As well, DNA from cultured cells or cell lines can be extracted and used as target DNA.

The target DNA may be used in the form isolated from the cells. Alternatively, the isolated DNA may be fragmented, for example, digested with one or more restriction enzymes, to yield smaller fragments of target DNA that may be easier to manipulate than unfragmented strands. The isolated DNA may also be used as a template and amplified using standard amplification methods as are known in the art, for example PCR amplification techniques or primer extension techniques. Preferably, a high fidelity enzyme and stringent conditions are used if amplification methods are performed, in order to minimize the introduction of errors into the sequence of the amplification product. The amplification product may then be used as target DNA in the present method.

The target DNA is hybridized with the probe DNA that is immobilized onto the surface 14 of sensor 10. If the target DNA is double-stranded, it will be necessary to melt the target DNA so as to provide single stranded DNA that will have a strand that contains a sequence complementary to the sequence of the probe DNA. Thus, typically the target DNA is heated to a temperature sufficient to melt the double-stranded DNA, for example, heating to 95° C. for 5 minutes, and contacted with the immobilized probe DNA at a temperature above the hybridization temperature, and allowed to cool so as to permit hybridization between the probe DNA and the target DNA strands. The hybridization temperature is chosen to be slightly below, for example 5 to 10° C. below, the theoretical temperature at which the probe DNA is predicted to hybridize to the target DNA, taking into account that the region of the mutation or polymorphism will not hybridize if the mutation or polymorphism is present in the target DNA.

The hybridization is performed in a suitable hybridization buffer. The conditions used, including the salt concentration, detergent type and concentration and temperature of hybridization, will vary depending on the length and sequence of the probe DNA and the degree of stringency required for hybridization. A skilled person will understand how to vary such conditions to achieve hybridization of a specific probe DNA to target DNA. The hybridization buffer will typically include magnesium ions for stabilization of the highly negatively charged DNA molecules.

Once hybridized, the probe/target DNA duplex, which is immobilized on the resonator sensor, is contacted with a mismatch binding molecule.

Most of the MBPs, for example MutS, recognize the 8 possible mismatch base pairings (A:A, A:C, A:G, C:C, C:T, G:G, G:T and T:T). Therefore, an MBP may be used as the mismatch binding molecule when all possible nucleotide substitutions, as well as insertions and deletions, are desired to be detected by the method. However, when a specific single nucleotide substitution is to be detected by the present method, an SMBL that is specific for that particular mismatch may be used.

If the target DNA does not contain a mutation, it will form a homoduplex upon hybridization with the probe DNA, and will not be specifically recognized by the mismatch binding molecule. However, if the target DNA does contain a mutation such that its sequence is different from that of the probe DNA, a heteroduplex will be formed upon hybridization, which can be specifically recognized and bound by the mismatch binding molecule.

The contacting of the mismatch binding molecule with the duplex DNA is performed in a buffer that will not disrupt the duplex DNA, and in which the mismatch binding molecule is stable, soluble, and able to interact specifically with mismatch DNA. The buffer will vary depending on the mismatch binding molecule used, and a skilled person will be able to determine suitable buffer conditions for a given mismatch binding molecule. If an MBP is used, the buffer should be such that the protein is not denatured or rendered inactive. As well, depending on the MBP, it may be pre-treated with any cofactors that influence the specificity of binding of the MBP. For example, the specificity of MutS for mismatch DNA is increased in the presence of ATP, as will be understood by a skilled person. Thus, pretreating MutS with ATP will minimize non-specific binding of MutS to the DNA backbone.

As will be appreciated by a skilled person, surface 14 of resonator sensor 10 may be rinsed between steps of the present method as desired. For example, surface 14 may be rinsed with blank buffer to remove any unbound mismatch binding molecule after contacting of mismatch binding molecule with hybridized probe DNA/target DNA, so as to remove any free mismatch binding molecule that may affect the measurements of the resonance parameters. A skilled person will be able to readily determine the desirability of rinsing, for example by including a control resonator sensor having homoduplex DNA immobilized on surface 14 to determine if rinsing is required to avoid a false positive measurement.

As will be appreciated, the resonance parameters may be measured both in dry state or liquid environments. For the former, any buffer solution employed is removed from surface 14 prior to measuring resonance parameters. Alternatively, the resonance parameters can be measured while surface 14 is in contact with a buffer under the same buffer conditions before and after binding of mismatch binding molecule.

Once the target DNA is hybridized with the probe DNA immobilized on surface 14 of sensor 10, and the mismatch binding molecule is allowed to bind to any existing heteroduplex DNA, changes to the resonance parameters can be measured and compared with resonance parameters as measured after duplex formation but before contacting with the mismatch binding molecule.

As noted, the resonance parameters of the resonator sensor are dependent on the combined mass of the vibrating element, an immobilized capture molecule and any molecule that may be hybridized and/or complexed with the capture molecule. Therefore, a change in the parameters will be observed upon binding of the mismatch binding molecule to the immobilized heteroduplex, if a mutation is present in the target DNA. Resonator sensors can measure mass loading, viscoelastic properties, and surface stress upon binding of a mismatch binding molecule to the immobilized heteroduplex DNA.

The resonator sensor is capable of measuring the various parameters of resonance vibration. Such parameters include the specific resonant frequency, the amplitude of oscillation, the phase of oscillation, the oscillation quality factor of oscillation and the damping property. The oscillation quality factor refers to the sharpness of resonance or frequency selectivity of a resonator sensor. That is, a high oscillation quality factor indicates that the resonator sensor is very selective for resonant frequency, and will resonate only within a very narrow range of frequencies. A low oscillation quality factor indicates that the resonator sensor responds to a wide range of frequencies surrounding the resonant frequency at which maximum amplitude is observed.

As the mass loaded on the vibrating element is increased, such as by the complexing of a mismatch binding molecule to an immobilized heteroduplex DNA, the resonant frequency will shift to a lower frequency, allowing for detection of any binding of the mismatch binding molecule to heteroduplex DNA. As described above, resonator sensors respond to changes of mechanical properties of the material contacting the surface of the sensor.

The damping of resonator sensor 10 can be used to indicate position of the mutation relative to the sequence of the probe DNA.

If an MBP such as MutS is used, the influence on the damping property factors by the binding of the mismatch binding molecule will vary depending on whether the binding is specific due to binding to a mismatch pairing, or whether it is non-specific due to interactions with the DNA backbone.

The mismatch binding molecule may be labelled, so as to enhance detection of binding by the mismatch binding molecule to heteroduplex DNA. The label may be a molecule or moiety that enhances detection of the mismatch binding molecule by increasing the mass on the resonator sensor surface. For example the label may be a heavy metal nanoparticle. Attachment of a heavy metal nanoparticle to a mismatch binding protein will add mass to the mismatch binding molecule, and increase the effect on the resonance parameters when the mismatch binding molecule is bound to heteroduplex DNA. The label may be an enzyme that cleaves a substrate to produce an insoluble product that precipitates and which precipitate is not removed when the buffer in which the cleavage reaction is performed is removed, such that the deposition of the precipitate increases the mass on the resonator sensor due to the presence of bound mismatch binding molecule. For example, the insoluble product may be a coloured or chemiluminescent molecule that precipitates.

As will be understood, where the mismatch binding molecule is labelled with an enzyme that cleaves a substrate, unbound mismatch binding molecule is first removed, including by rinsing surface 14 prior to adding cleavage buffer and substrate so that a precipitate is formed only where mismatch binding molecule is bound to hybridized probe DNA/target DNA. However, as will be understood, there could remain unbound mismatch binding molecule at levels which would not result in any detectable increase in mass once the substrate is added.

Once a given target DNA has been tested, the resonator sensor 10 with immobilized probe DNA can be regenerated for confirmation of binding with the same or different mismatch binding molecule or for reuse with a new target DNA, using conditions that will disrupt interaction between the mismatch binding molecule, and if desired, the interaction between duplex DNA and between the target DNA and the immobilized probe DNA. For example, bound MutS protein may be removed by washing with a buffer containing no EDTA and dithiolthreitol (DTT), which are essential components required for MutS binding activity. The duplex DNA may be dissociated by passing washing with a buffer containing denaturants such as dilute HCl, dilute NaOH, or detergents such as SDS. Such denaturants will interrupt the base pairing of the DNA duplex, removing the target DNA and leaving the immobilized probe DNA available for hybridization with another target DNA. By means of this recycling technique, comparison of loading of mismatch binding molecule onto heteroduplex or homoduplex DNA can be made without the need to correct for varying probe DNA density on the resonator sensor 10.

Therefore, where a mutation is detected, the measurement may be repeated by contacting the mismatch binding molecule to recycled heteroduplex DNA in the presence and absence of specific dNTPs, to determine which bases are unpaired in a heteroduplex DNA, so as to assist in determining the nature of the mutation. Particular combinations of paired dNTPs may be added to immobilized duplex DNA, and will pair with any unpaired complementary bases that are present in the duplex DNA. For example, if the target DNA contains an A→G substitution that results in a T:G mismatch base pairing in the duplex DNA, dATP and dCTP can be contacted with the immobilized hybridized DNA prior to contacting of the mismatch binding molecule. The binding of the dATP to the unpaired T and the dCTP to the unpaired G will leave no binding site for the mismatch binding molecule.

A skilled person will appreciate that in the present method, capture molecule 16 immobilized on surface 14 of sensor 10 may alternatively be a mismatch binding molecule. Thus, a mutation in a target DNA can be detected by hybridizing a target DNA with a probe DNA and contacting the hybridized probe/target DNA with a mismatch binding molecule, which is immobilized on sensor 10.

The hybridization between the probe DNA and target DNA is generally performed as described above, except that it is done apart from resonator sensor 10. The duplex DNA, once hybridized, is then contacted with the immobilized mismatch binding molecule using a suitable buffer that will not disrupt the duplex DNA or the mismatch binding activity, as described above.

Measuring the resonance parameters, or obtaining a measurement of a resonance parameter of resonator sensor 10 where capture molecule 16 is a mismatch binding molecule, prior to contacting with hybridized probe DNA/target DNA may be performed immediately prior to the contacting. However, a skilled person will understand that, depending on the particular resonance parameter being measured and on the type of resonator sensor used, this measurement may be obtained earlier, for example, from a manufacturer or supplier of resonator sensor 10 onto which the mismatch binding molecule is immobilized. However, it is preferred to obtain the first measurement under the same environmental and equipment conditions as for obtaining the second measurement, since the resonance parameters can be sensitive to environmental conditions such as temperature, humidity, etc.

The probe DNA may be also be labelled with a molecule or moiety that allows for detection of binding of the heteroduplex DNA by the mismatch binding molecule by increasing the mass on the resonator sensor surface, as described above for labelling of the mismatch binding molecule.

This approach of immobilizing the mismatch binding molecule is suitable for polymorphism detection which involves target DNA containing long DNA fragments, since binding of a larger heteroduplex DNA will produce a shift in frequency response that is more readily detected than that produced by binding of a smaller heteroduplex DNA molecule.

The present methods allow for rapid detection of mutations, for example those associated with DNA polymorphisms including single base substitutions within a nucleotide sequence. These methods do not require the use of electrophoresis techniques, which are time-consuming and usually require time-consuming staining procedures or detection of labelled species. As such, the present methods are well suited for high throughput processing and easy handling of a large number of DNA samples. To assist in high volume processing of samples, the present methods may be adapted for resonator sensor arrays.

Figure 2:
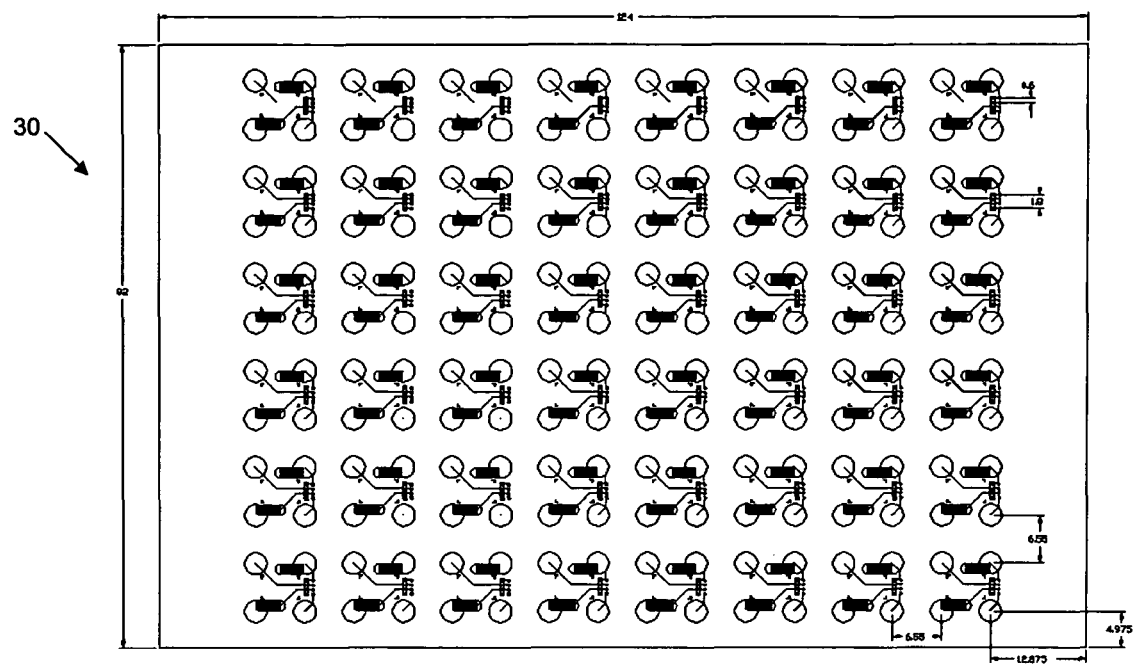
FIG. 2 is a schematic diagram of an array of resonator sensors arranged in a 48-well microtitre plate.
Figure 3:
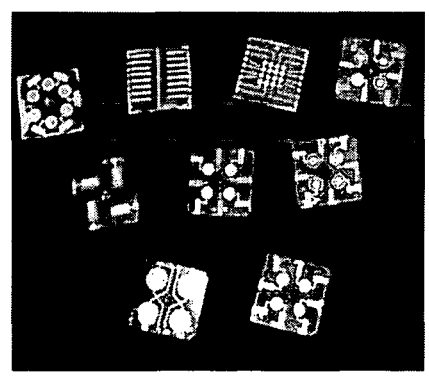
FIG. 3 is a photograph of arrays of piezoelectric quartz crystal-based resonator sensors in which QCM sensors are arrayed on quartz.

Thus, multiple resonator sensors 10 can be arranged into an array 30. FIG. 2 depicts a schematic of an array 30 in which multiple resonator sensors 10, for example QCM-D resonator sensors, are arranged within a 48-well micro-titre plate. FIG. 3 is a photograph of arrays of quartz type resonator sensors 10 that can be used with microfluidic cells. The use of microfluidic cells allows for a number of resonator sensors 10 to be arranged into a small area.

Preferably, each resonator sensor 10 is located within a discrete compartment, for ease of applying the same or different capture molecule 16 and target DNA to each surface 14 of each vibrating element 12 of each resonator sensor 10. An automated system can be used to apply and remove fluids and sample to each resonator sensor 10.

Depending on the type of resonator sensor 10 used, the array 30 may be arranged so that an independent excitation source 20 and independent motion sensor 22 and detector 24 is used to drive and detect the vibration of each vibrating element 12. However, a single excitation source 20, or a single motion sensor 22 and detector 24 may be used with multiple resonator sensors 10 within array 30. For example, for a quartz crystal microbalance array, a separate electronic drive circuit may be coupled to each sensor in the array, with each of the drive circuits coupled to a counter/timer or spectrum analyser in order to detect shifts in the frequency response. For arrays of resonator sensors for which optical detection of frequency response is used, a single detector which then reads each sensor individually may be used.

A different probe DNA having a unique sequence that allows for detection of a given mutation may be immobilized on the surface 14 of respective sensors 10. Each probe DNA immobilized in the array 30 may then be contacted with the same target DNA. In this way it is possible to screen one target DNA for a large number of possible mutations or polymorphisms at one time.

Alternatively, multiple resonator sensors 10 may be arranged in an array 30 such that each individual resonator sensor has the same probe DNA immobilized onto its surface 14. A different target DNA is hybridized with the probe DNA on each respective resonator sensor 10. In this way a large number of target DNAs may be screened for a particular mutation or polymorphism.

Multiple resonator sensors 10 within array 30 may also have a different mismatch binding molecule immobilized on surface 14 of each resonator sensor 10, where each mismatch binding molecule is selective for a particular mismatch. Such an array is useful for screening a single probe DNA hybridised with the same target DNA for specific mutations.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

EXAMPLES

In the following examples, a bulk acoustic wave device, particularly a quartz crystal microbalance (QCM), was used as one example of the resonator sensor. AT-cut, 10 MHz quartz crystals with gold electrodes (5.1 mm) on both sides were used. These crystals provided mass sensitivity of 4.4 ng·cm$^{-2}$·Hz$^{-1}$ for a rigid, evenly distributed and sufficiently adsorbed layer. The resonant frequency was measured using the PzTools™ hardware and software from the Universal Sensors, Inc. (Metairie, La., USA) and the motional resistance was measured by a network analyzer (S&A 250B Network Analyzer, Saunders and Associates, Inc. USA).

Thermostable MutS protein from the thermophilic bacterium *Thermus aquaticus* (Epicentre Technologies, Corp.) was used as an example of the mismatch binding protein. This protein was supplied in a 50% glycerol solution containing 50 mM Tris-HCl (pH 7.5), 100 mM NaCl, 1 mM dithiolthreitol, 0.1 mM EDTA and 0.1% Triton X-100. Single stranded DNA binding protein (SSB) (Amersham Bioscience Limited) and BSA (Sigma-Aldrich, St. Louis, Mo.) were used to minimize non-specific MutS binding. Streptavidin (Sigma-Aldrich, St. Louis, Mo.)-biotin chemistry was used to immobilize biotinylated DNA probes on to the surface of the resonator.

Highly purified salt free (HPSF) oligonucleotides were from MWG (Germany). The sequences of the oligonucleotides (see Table 1 below) were taken from the 30 base regions surrounding the site of the sickle cell mutation in the human β-globin gene. Both the oligonucleotides having the sequences identified as SEQ ID NO.:1 and SEQ ID NO.:4 were prepared with a biotin label at the 5' end and served as probes (probe 1 and probe 4) to be immobilized onto the streptavidin-modified surface. The oligonucleotide having the sequence of SEQ ID NO.:2 is fully complementary to probe 1 and the oligonucleotide having the sequence of SEQ ID NO.:3 contains a single base substitution (A→G) at the center, forming a T:G mismatch with probe 1 (underlined in Table 1). The oligonucleotides having the sequences of SEQ ID NO.:5 to SEQ ID NO.:8 are complementary to probe 4 but contained one to four bases insertions, which are underlined in Table 1.

TABLE 1

OLIGONUCLEOTIDE SEQUENCES FOR DUPLEX DNA FORMATION

| Nucleotide Sequence | SEQ ID NO.: |
|---|---|
| Homoduplex DNA | |
| 5'-GCACCTGACTCCTGTGGAGAAGTCTGCCGT-3' | 1 |
| 3'-CGTGGACTGAGGACACCTCTTCAGACGGCA-5' | 2 |
| T:G Mismatch | |
| 5'-GCACCTGACTCCTGTGGAGAAGTCTGCCGT-3' | 1 |
| 3'-CGTGGACTGAGGAC<u>G</u>CCTCTTCAGACGGCA-5' | 3 |
| Insertion | |
| 5'-ACGGCAGACTTCTCCCCAGGAGTCAGGTGC-3' | 4 |
| 3'-TGCCGTCTGAAGAGG<u>C</u>CGGTCCTCAGTCCACG-5' | 5 |
| 5'-ACGGCAGACTTCTCCCCAGGAGTCAGGTGC-3' | 4 |
| 3'-TGCCGTCTGAAGAGG<u>AC</u>GGTCCTCAGTCCACG-5' | 6 |
| 5'-ACGGCAGACTTCTCCCCAGGAGTCAGGTGC-3' | 4 |
| 3'-TGCCGTCTGAAGAGG<u>GAC</u>GGTCCTCAGTCCACG-5' | 7 |
| 5'-ACGGCAGACTTCTCCCCAGGAGTCAGGTGC-3' | 4 |
| 3'-TGCCGTCTGAAGAGG<u>GGAC</u>GGTCCTCAGTCCACG-5' | 8 |

Figure 4:
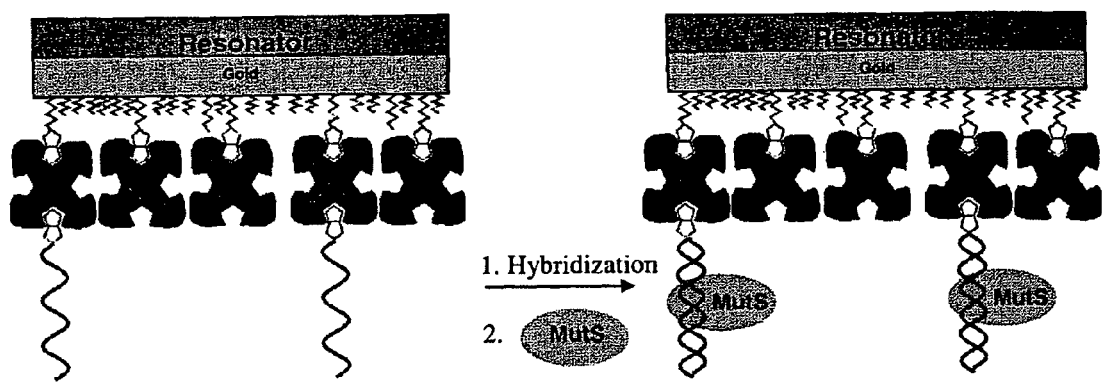
FIG. 4 is a schematic diagram of a the hybridization of a target DNA and subsequent binding of mismatch binding protein MutS to probe DNA immobilized on a resonator sensor using biotin/streptavidin interactions.
Figure 5:
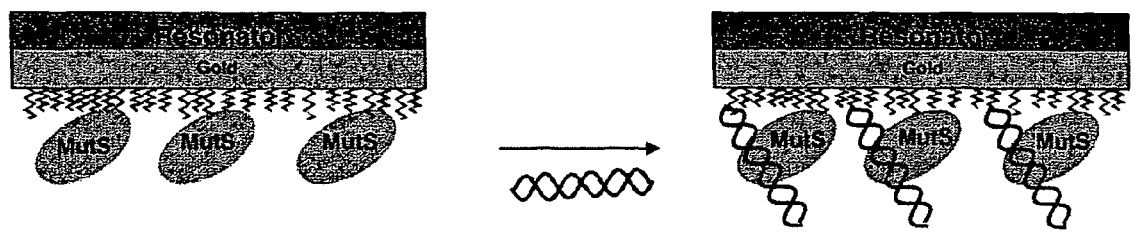
FIG. 5 is a schematic diagram of the binding of heteroduplex DNA by MutS protein immobilized on a resonator sensor.

FIGS. 4-5 are schematic representations of the methods used in the following Examples. FIG. 4 depicts the biotin/streptavidin immobilization of probe DNA onto the resonator, as described in Examples 1-3 and FIG. 5 depicts the immobilization of MutS protein, as described in Example 4.

Example 1

Figure 6:
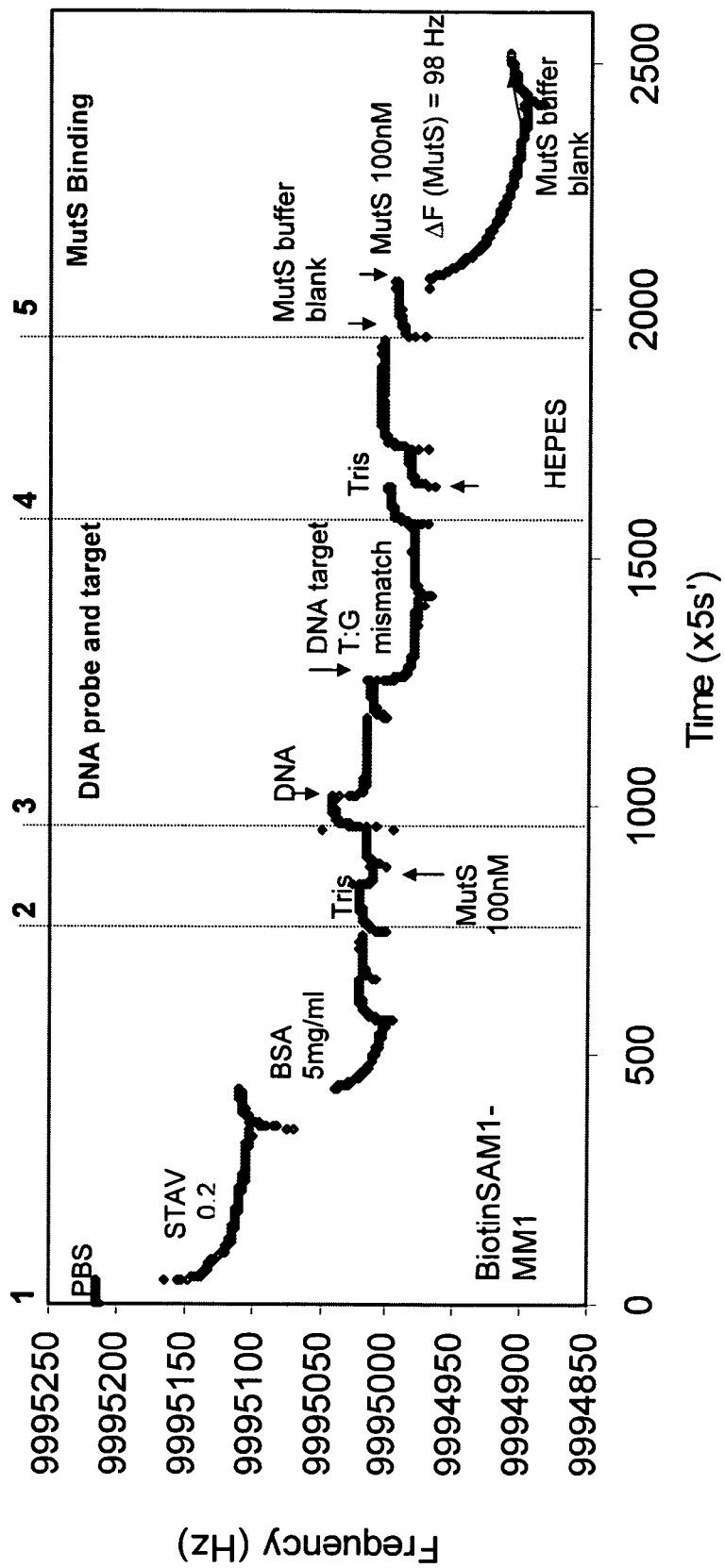
FIG. 6 illustrates the frequency response of a biotin-thiol modified resonator sensor (QCM) to the binding of MutS to heteroduplex DNA containing a T:G mismatch, in which the frequency response curve is shown from fabrication of the streptavidin film, through biotin-DNA assembly, hybridization of target DNA, to MutS binding.

Detection of G:T Mismatch using Method I: FIG. 6 shows the frequency response of a QCM to a whole reaction procedure using the method depicted in FIG. 4, starting from a biotin-thiol treated surface.

Briefly, streptavidin in PBS buffer (0.1 mg/ml) was immobilized on a surface which was first reacted with a biotin-thiol molecule based on biotin-streptavidin interaction. BSA was then applied (5 mg/ml in PBS) to block any possible free gold surface that might be present due to the low biotin self-assembled monolayer coverage. The baseline was determined using circulated Tris-HCl buffer (20 mM Tris-HCl, pH 7.5, 200 mM NaOH, 1 mM DTT, 0.1 mM EDTA, and 5 mM MgCl$_2$), followed by MutS buffer blank alone, which contains the same amount of glycerol and Triton™ X-100 as in the MutS protein sample, which further contains MutS at a final concentration of 100 nM (diluted 1:200 from the stock buffer, using Tris-HCl buffer). The subsequent application of the MutS protein produced a barely detectable frequency response, indicating that there are negligible levels of non-specific binding.

After switching the carrier buffer to HEPES, biotinylated probe 1 was applied (1 μM). After equilibrium, HEPES buffer was injected to rinse and remove unloaded probe. Targeted DNA sample (SEQ ID NO.:2 or SEQ ID NO.:3) (5 μM) was then added and allowed to hybridize at room temperature. HEPES buffer was then injected to rinse the surface of the QCM. The resulting dsDNA was referred as mismatch 0 ("MM0") or mismatch 1 ("MM1"), respectively.

The buffer was exchanged from HEPES to Tris-HCl was repeated after the formation of dsDNA. Since there were no detectable loss of targeted DNA upon the buffer exchange, Tris-HCl was then used as the carrier buffer for the subsequent MutS-DNA complex formation. Since the MutS protein was stored in Tris buffer with 50% highly viscous glycerol and 0.1% triton X-100, the small amount of glycerol and triton X-100 in the diluted protein solution (for example 1:200 dilution) resulted in a detectable frequency response. To eliminate the effect of viscosity change effect during the MutS binding, MutS buffer blank was prepared. A new baseline was created by this buffer at the same dilution as the protein solution. The subsequent binding signal upon MutS application was attributed to the mismatch recognition. After the MutS binding, the same buffer blank was applied to rinse loosely bound protein.

Figure 7:
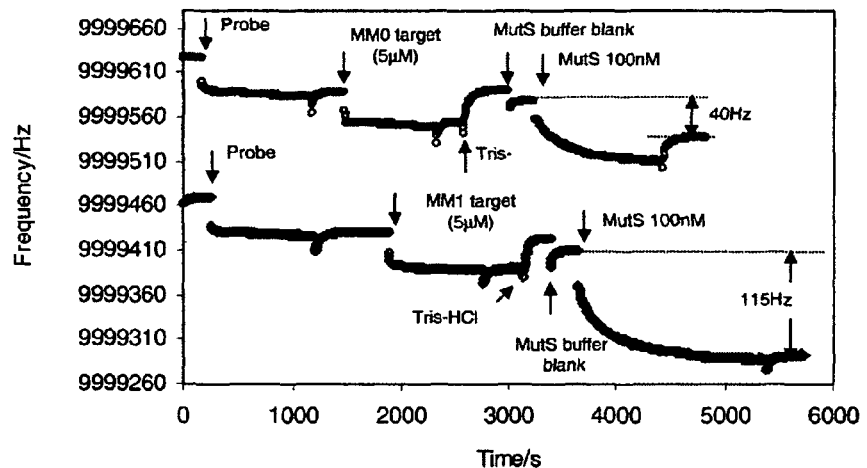
FIG. 7 illustrates the frequency response of a QCM to the binding of MutS to homoduplex DNA (MM0) as compared to heteroduplex DNA containing a T:G mismatch (MM1)

FIG. 7 is a comparison of the formation of MM1 and MM0 DNA and the subsequent MutS binding. The single base substitution in the target DNA did not result in detectable discrimination during the hybridization, while the subsequent MutS binding showed a clear difference in both binding amount and profile (association and dissociation). The observation of the MutS binding on MM0 DNA was not surprising as the clamp domains in the MutS protein has certain contact with the DNA backbone in a non-specific manner (Lamers et al., *Nature* 2000, 407, 711-717). This contact is however weaker than the hydrogen bonds formed in the heteroduplex DNA-MutS complex. Upon rinsing, the frequency tended to rise back to the baseline levels. To eliminate the unwanted MutS adsorption with MM0 DNA, one can use ATP to modulate the MutS specificity, by pre-incubating the MutS protein with 20 mM ATP. The ATP-treated MutS binds only to the mismatched DNA but not to the MM0 DNA.

A titration experiment indicated that the probe-immobilized sensor could sense the hybridized DNA (both MM1 and MM0) down to the concentration of 5 nM. At any concentration in the range from 5 μM to 5 nM, discrimination of the MutS binding signal to MM1 and MM0 DNA was obtained. Since at low target concentration the immobilized probe was not saturated, the MutS binding signal was attributed to both the mismatch recognition and nonspecific adsorption on ssDNA. For MM1 target at 50 nM for example, it was believed that only ~30% of the ssDNA probe was occupied.

The direct application of MutS right after hybridization resulted in a 95 Hz of frequency shift. In a comparison experiment, SSB (400 nM) was applied to block the remaining ssDNA probe. The subsequent MutS binding resulted in only 78 Hz of frequency response. If the discrimination of the MM1 and MM0 is the concern, one can ignore the nonspecific adsorption issue as the difference in signal is low (a direct MutS adsorption signal on ssDNA without target hybridization was not more than 30 Hz) and occurs equally in both cases. If one wants to know exactly the mismatch recognition signal, it is necessary to block the surface with SSB.

When the concentration of the target DNA was further lowered down to where the hybridization was not detectable, for example at 0.5 nM, MutS binding on MM1 was still significantly detectable when compare to that on MM0 DNA at the same concentration.

Example 2

Figure 8:
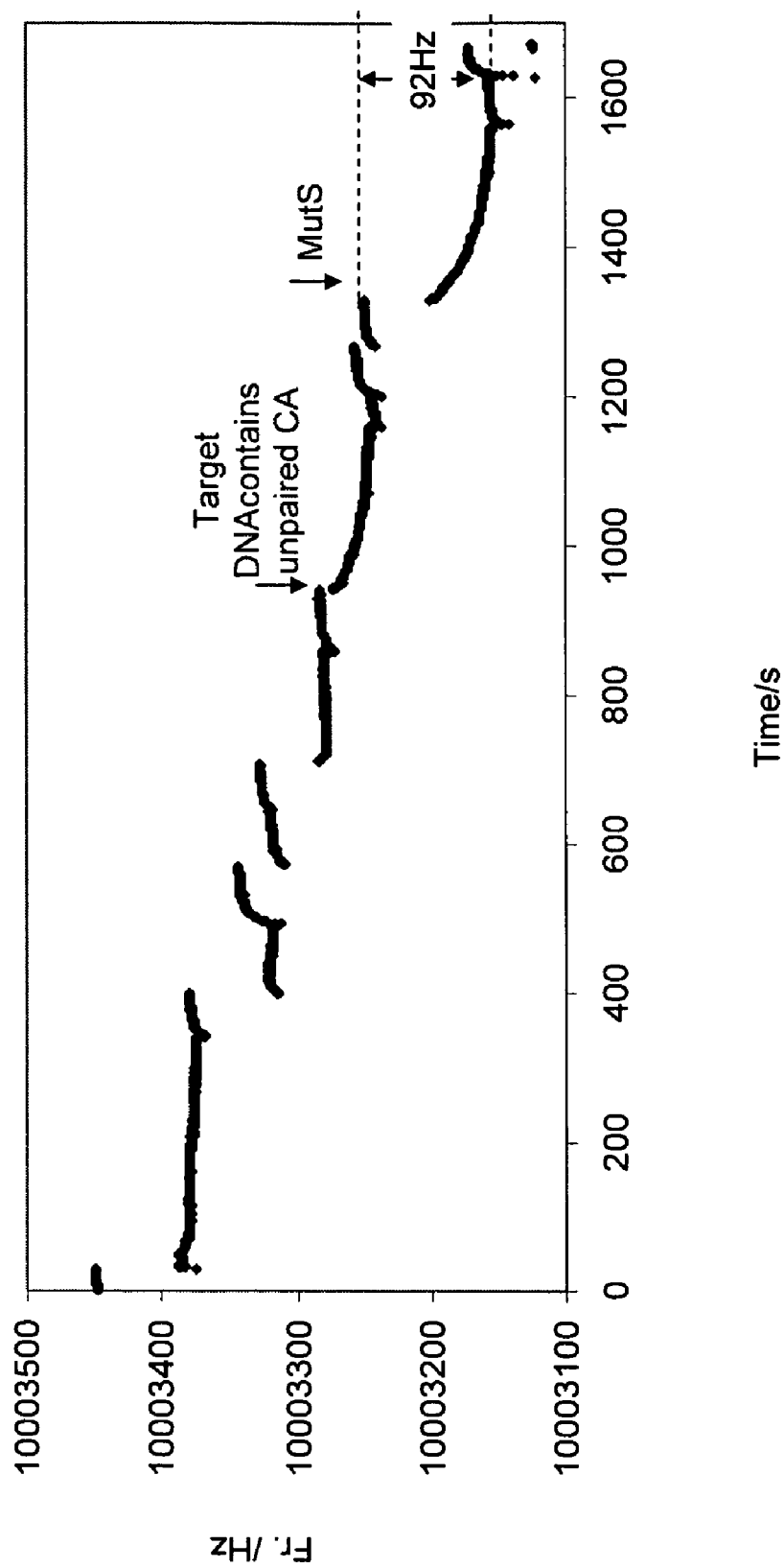
FIG. 8 illustrates the frequency response of a QCM to the binding of MutS to heteroduplex DNA containing an unpaired CA.
Figure 9:
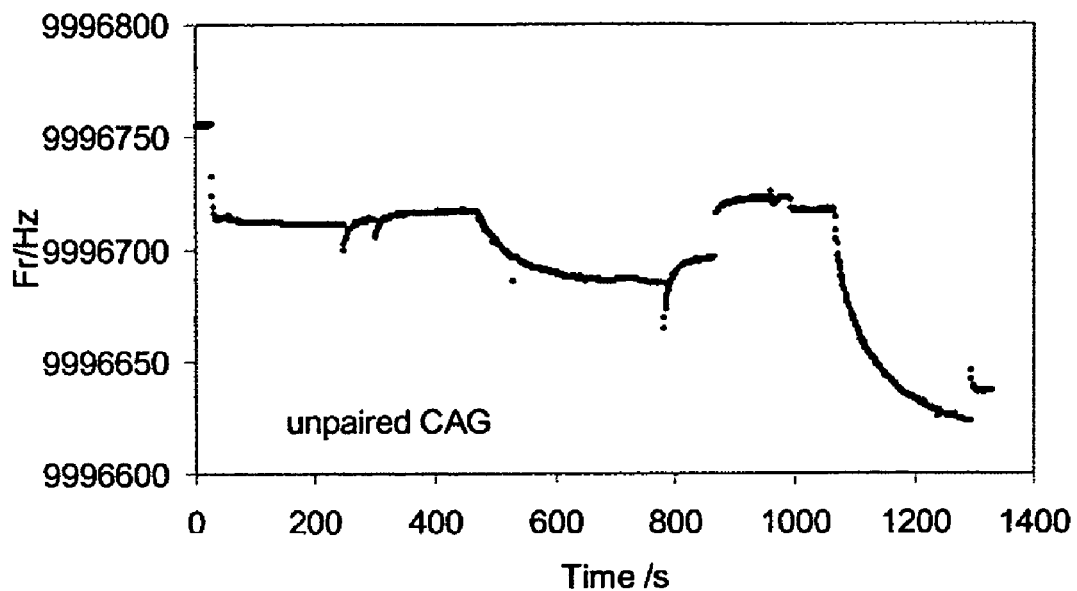
FIG. 9 illustrates the frequency response of a QCM to the binding of MutS to heteroduplex DNA containing an unpaired CAG.

Detection of 1 to 4 Deletions: In this example, probe 4 was immobilized and target DNAs (SEQ ID NOS.:5 to 8) (1 uM) were hybridized to form heteroduplexes containing 1 to 4 unpaired bases. Again, the hybridization profile between the MM0 and unpaired DNA showed no significant difference, while the subsequent MutS binding shows obvious difference in both the binding amount and binding kinetics. The consequent response frequency upon MutS binding these DNA was 92 Hz (unpaired CA), 90 Hz (unpaired C), 76 Hz (unpaired CAG), and 70 Hz (unpaired CAGG), which indicates that heteroduplexes containing 1 to 4 unpaired bases were detectable, but not equally well. This is likely due to differing binding affinities of MutS, resulting in different saturation amounts of MutS on each heteroduplex. The order of the detection sensitivity appeared to be 2 unpaired bases$\geq$1 unpaired base>3 unpaired bases>4 unpaired bases. For the heteroduplex with 3 or 4 unpaired bases, the MutS binding was less stable, since rinsing with Tris buffer could result in significant loss of protein (FIGS. 8 and 9).

Example 3

Figure 10:
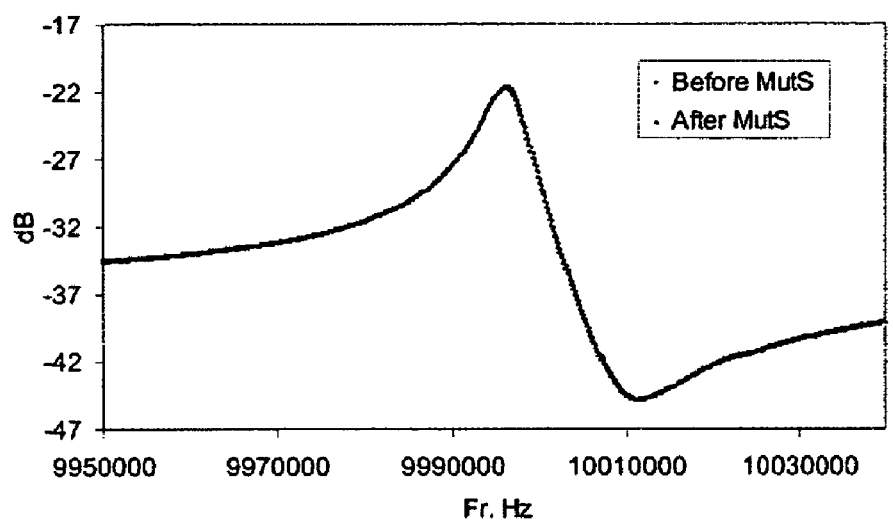
FIG. 10 is a frequency spectrum of a QCM with immobilized probe DNA hybridized in a heteroduplex before and after binding of MutS protein.
Figure 11A:
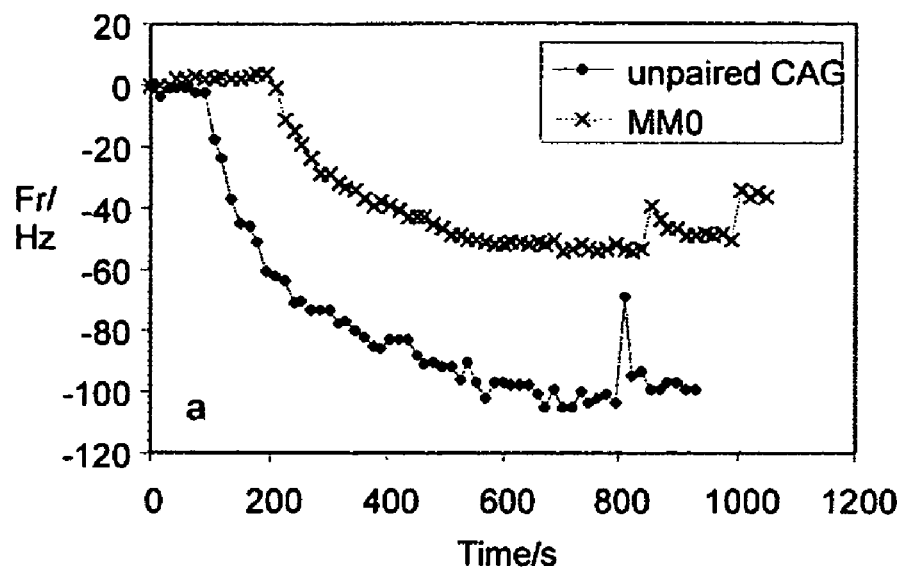
FIG. 11A-B are graphs illustrating the changes in frequency (A) and motional resistance (B) upon MutS binding to immobilized heteroduplex DNA containing a T:G mismatch or an unpaired CAG.
Figure 11B:
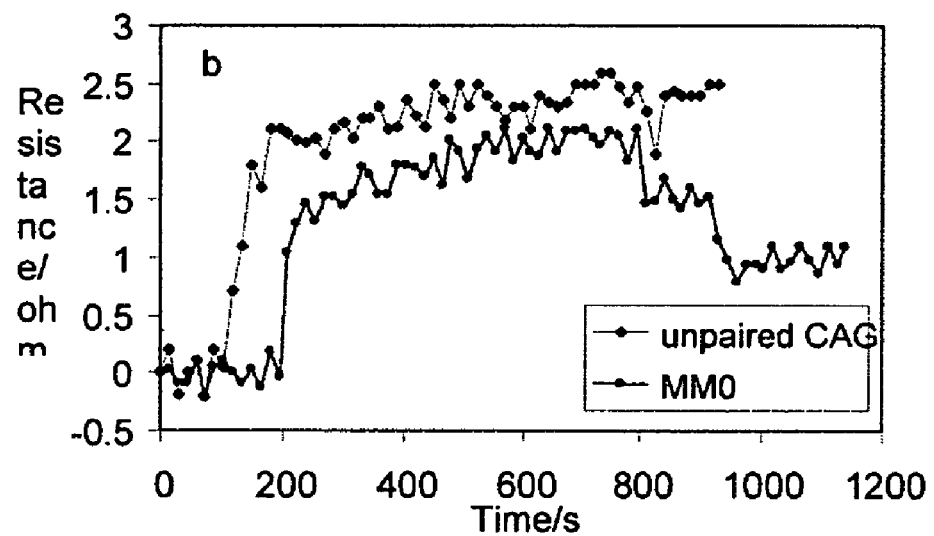

Motional Resistance Measurement of MutS Binding: In this experiment, the QCM sensor carrying a DNA heteroduplex containing two unpaired bases, CA, was connected to an S&A 250B Network Analyzer (Saunders & Associates, Inc., USA). The oscillation spectrum of the QCM before and after MutS binding was recorded (FIG. 10). FIG. 11 shows the kinetic curves of the frequency (A) and motional resistance (B) changes upon MutS binding on the unpaired CA DNA and a homoduplex DNA. The ratio between $\Delta R$ and $\Delta F$ for the MM0 (0.033) was greater than that for the unpaired CA (0.025). This difference is believed to relate to the different nature of the MutS binding to homoduplex DNA as compared to heteroduplex DNA. The adsorbed protein based on non-specific contact with the MM0 DNA backbone tends to be more flexible when compare to that based on unpaired bases recognition.

Example 4

Figure 12:
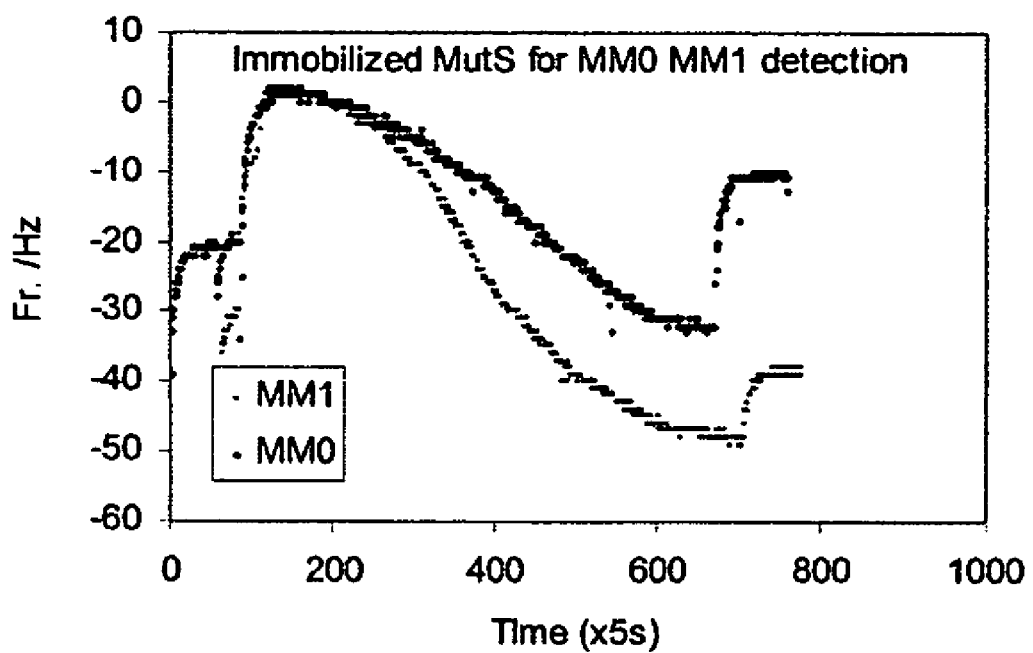
FIG. 12 is graph illustrating the frequency response of a QCM with immobilized MutS bound to either MM0 (mismatch 0, homoduplex) or MM1 (mismatch 1, heteroduplex) DNA.

Detection of G:T mismatch: In this method, as depicted in the schematic of FIG. 5, the MutS protein was immobilized on a gold electrode by physical adsorption. A thin polystyrene film was prepared on the electrode by dropping 5 µl of polystyrene solution (5 mg/ml in toluene) on to the electrode. Upon evaporation of the solvent, a thin layer of polystyrene was left behind. The resulting film was heated for 10 min at 90° C. to enhance the adhesion. 10 ul of MutS solution (400 nM in Tris-HCl buffer) was applied for incubation for 2 hours. After washing and drying the surface, the amount of the immobilized MutS protein can be calculated through the frequency change.

dsDNA was prepared in solution. The same amount of oligonuleotides SEQ ID NOS.:1 and 2 and SEQ ID NOS.:2 and 3 were mixed together. The mixtures were heated at 90° C. for 10 min to remove the possible secondary structures. The solutions were then allowed to cool down to room temperature slowly and the MM0 and MM1 dsDNA formed. The QCM carrying the MutS protein was the exposed to tris-HCl. Upon equilibrium, the MM0 DNA was applied. Over a period of ~50 minute the frequency drop was 30 Hz which might be caused by nonspecific binding. For a MM1 DNA, the frequency drop was 48 Hz. After rinsing the MM0 DNA was removed greatly while the MM1 DNA did not loss too mush as the DNA-MutS complex is stable enough (FIG. 12) and the difference between MM1 and MM0 signal became more was significant with a factor of 3.5.

As can be understood by one skilled in the art, many modifications to the exemplary embodiments described herein are possible. The invention, rather, is intended to encompass all such modification within its scope, as defined by the claims.

What is claimed is:

1. A method of detecting a mutation in a target DNA comprising: obtaining a first measurement of a resonance parameter of a resonator sensor, said resonator sensor having a vibrating element, said vibrating element having a surface, and a probe DNA immobilized on said surface, said probe DNA hybridized with a target DNA; contacting the hybridized probe DNA and target DNA with a mismatch binding molecule in order to form a mismatch binding molecule/duplex DNA complex; obtaining a second measurement of the resonance parameter of the resonator sensor; comparing the first and second measurement of the resonance parameter to detect formation of the mismatch binding molecule/duplex DNA complex; determining if the mismatch binding molecule bound to the duplex DNA due to binding to a mismatch pairing or if the mismatch binding molecule bound to the duplex DNA due to nonspecific interactions with the duplex DNA backbone; and detecting the presence of a mutation in the target DNA when it is determined that the mismatch binding molecule bound to the duplex DNA due to binding to a mismatch pairing.

2. The method of claim 1 wherein the resonator sensor comprises a bulk acoustic wave device, a quartz crystal microbalance, a surface acoustic wave device, a flexural wave plate, a piezoelectric thin film, a quartz tuning fork, a MEMS resonator, a membrane, a bridge, a suspended masses or a cantilever.

3. The method of claim 1 wherein obtaining comprises measuring resonant frequency, impulse response, resonance amplitude, phase, quality factor, damping property, energy dissipation, response spectrum or sharpness of resonance.

4. The method of claim 1 wherein the mutation is a single base substitution, a deletion of 1 to 4 bases, or an insertion of 1 to 4 bases.

5. The method of claim 1 wherein the target DNA is extracted from a cell from a patient.

6. The method of claim 5 wherein the cell is a blood cell, a skin cell, a liver cell, a kidney cell, a lung cell, a breast cell or a tumour cell.

7. The method of claim 1 wherein the mismatch binding molecule is a mismatch binding protein.

8. The method of claim 7 wherein the mismatch binding protein is MutS from *Escherichia coli, Salmonella typhimurium* or *Thermus aquaticus*, or HexA from *Streptococcus pneumoniae*.

9. The method of claim 1 wherein the mismatch binding molecule is a synthetic mismatch binding ligand.

10. The method of claim 9 wherein the synthetic mismatch binding ligand is a naphthyridine dimer, a naphthyridine-azaquinolone hybrid or an aminonaphthyridine dimer.

11. The method of claim 1 wherein the probe DNA comprises a non-disease sequence of a genetic marker.

12. The method of claim 11 wherein the genetic marker is a marker for cancer, atherosclerosis, heart disease, diabetes, cystic fibrosis or Alzheimer's disease.

13. The method of claim 1 wherein the probe DNA is immobilized on the surface of the vibrating element through a reactive functional group attached at one end of the probe DNA.

14. The method of claim 13 wherein the reactive functional group is a thiol group, amino group, carboxylic acid group, hydroxyl group, phenol group or phosphate group.

15. The method of claim 1 wherein the probe DNA is immobilized on the surface of the vibrating element through an affinity binding molecule attached at one end of the probe DNA.

16. The method of claim 15 wherein the affinity binding molecule is biotin, streptavidin, avidin, an ATP analogue, an ATP binding domain, or a 6-histidine peptide.

17. The method of claim 1 wherein the mismatch binding molecule is labeled with a heavy metal nanoparticle.

18. The method of claim 1 where the mismatch binding molecule is labeled with an enzyme that cleaves a substrate to produce an insoluble product.

19. The method of claim 1 wherein the resonator sensor comprises a plurality of resonator sensors arranged in an array and a different probe DNA is immobilized on a surface of a vibrating element of each resonator sensor in the array, and wherein each probe DNA is hybridized with the same target DNA.

20. The method of claim 1 wherein the resonator sensor comprises a plurality of resonator sensors arranged in an array and the same probe DNA is immobilized on a surface of a vibrating element of each resonator sensor in the array, and wherein a different target DNA is hybridized with the probe DNA on said surface of said vibrating element of said each resonator sensor.

21. A method of detecting a mutation in a target DNA comprising: obtaining a first measurement of a resonance parameter of a resonator sensor, said resonator sensor having a vibrating element, said vibrating element having a surface, and a mismatch binding molecule immobilized on said surface; contacting the mismatch binding molecule with a hybridized probe DNA and target DNA in order to form a mismatch binding molecule/duplex DNA complex; obtaining a second measurement of the resonance parameter of the resonator sensor; comparing the first and second measurement of the resonance parameter to detect formation of the mismatch binding molecule/duplex DNA complex; determining if the mismatch binding molecule bound to the duplex DNA due to binding to a mismatch pairing or if the mismatch binding molecule bound to the duplex DNA due to nonspecific interactions with the duplex DNA backbone; and detecting the presence of a mutation in the target DNA when it is determined that the mismatch binding molecule bound to the duplex DNA due to binding to a mismatch pairing.

22. The method of claim 21 wherein the resonator sensor comprises a bulk acoustic wave device, a quartz crystal microbalance, a surface acoustic wave device, a flexural wave plate, a piezoelectric thin film, a quartz tuning fork, a MEMS resonator, a membrane, a bridge, a suspended masses or a cantilever.

23. The method of claim 21 wherein obtaining comprises measuring resonant frequency, impulse response, resonance amplitude, phase, quality factor, damping property, energy dissipation, response spectrum or sharpness of resonance.

24. The method of claim 21 wherein the mutation is a single base substitution, a deletion of 1 to 4 bases, or an insertion of 1 to 4 bases.

25. The method of claim 21 wherein the target DNA is extracted from a cell from a patient.

26. The method of claim 25 wherein the cell is a blood cell, a skin cell, a liver cell, a kidney cell, a lung cell, a breast cell or a tumour cell.

27. The method of claim 21 wherein the mismatch binding molecule is a mismatch binding protein.

28. The method of claim 27 wherein the mismatch binding protein is MutS from *Escherichia coli, Salmonella typhimurium* or *Thermus aquaticus*, or HexA from *Streptococcus pneumoniae*.

29. The method of claim 21 wherein the mismatch binding molecule is a synthetic mismatch binding ligand.

30. The method of claim 29 wherein the synthetic mismatch binding ligand is a naphthyridine dimer, a naphthyridine-azaquinolone hybrid or an aminonaphthyridine dimer.

31. The method of claim 21 wherein the probe DNA comprises a non-disease sequence of a genetic marker.

32. The method of claim 31 wherein the genetic marker is a marker for cancer, atherosclerosis, heart disease, diabetes, cystic fibrosis or Alzheimer's disease.

33. The method of claim 21 wherein the mismatch binding molecule is immobilized on the surface of the vibrating element of the resonator sensor through a reactive functional group on the mismatch binding molecule.

34. The method of claim 33 wherein the reactive functional group is a thiol group, amino group, carboxylic acid group, hydroxyl group, phenol group or phosphate.

35. The method of claim 21 wherein the mismatch binding molecule is immobilized on the surface of the vibrating element of the resonator sensor through an affinity binding molecule attached to the mismatch binding molecule.

36. The method of claim 35 wherein the affinity binding molecule is biotin, streptavidin, avidin, an ATP analogue, an ATP binding domain, or a 6-histidine peptide.

37. The method of claim 21 wherein the mismatch binding molecule is immobilized through physical adsorption to the surface of the vibrating element of the resonator sensor.

38. The method of claim 37 wherein the surface of the vibrating element is coated with a polymer film.

39. The method of claim 38 wherein the polymer film is nitrocellulose, polystyrene, polyethylene, or nylon.

40. The method of claim 21 wherein the probe DNA is labeled with a heavy metal nanoparticle.

41. The method of claim 21 where the probe DNA is labeled with an enzyme that cleaves a substrate to produce an insoluble product.

42. The method of claim 21 wherein the resonator sensor comprises a plurality of resonator sensors arranged in an array and a different mismatch binding molecule is immobilized on a surface of a vibrating element of each resonator sensor in the array and wherein the same hybridized probe DNA and target DNA is contacted with each mismatch binding molecule.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 1
gcacctgact cctgtggaga agtctgccgt                                    30

<210> SEQ ID NO 2
<211> LENGTH: 30
<212> TYPE: DNA
<213> ORGANISM: Artificial sequence
<220> FEATURE:
```

-continued

<223> OTHER INFORMATION: synthetic oligonucleotide

<400> SEQUENCE: 2
acggcagact tctccacagg agtcaggtgc           30

<210> SEQ ID NO 3
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 3
acggcagact tctccgcagg agtcaggtgc           30

<210> SEQ ID NO 4
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 4
acggcagact tctccccagg agtcaggtgc           30

<210> SEQ ID NO 5
<211> LENGTH: 31
<212> TYPE: DNA
<213> ORGANISM: Artificial sequence
<220> FEATURE:
<223> OTHER INFORMATION: synthetic oligonucleotide

<400> SEQUENCE: 5
gcacctgact cctggcggag aagtctgccg t           31

<210> SEQ ID NO 6
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 6
gcacctgact cctggcagga gaagtctgcc gt           32

<210> SEQ ID NO 7
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 7
gcacctgact cctggcaggg agaagtctgc cgt           33

<210> SEQ ID NO 8
<211> LENGTH: 34
<212> TYPE: DNA
<213> ORGANISM: Artificial sequence
<220> FEATURE:
<223> OTHER INFORMATION: synthetic oligonucleotide

<400> SEQUENCE: 8
gcacctgact cctggcaggg gagaagtctg ccgt           34